(12) United States Patent
Arimoto et al.

(10) Patent No.: US 6,942,882 B2
(45) Date of Patent: Sep. 13, 2005

(54) HEPATIC DISORDER SUPPRESSANT

(75) Inventors: Yasushi Arimoto, Nasu-gun (JP);
Hiroyuki Suganuma, Nasu-gun (JP);
Takahiro Inakuma, Nasu-gun (JP);
Kimio Sugiyama, Shimizu (JP); He Puming, Shizuoka (JP); Hirokazu Kawagishi, Shizuoka (JP)

(73) Assignee: Kagome Co., Ltd., Aichi (JP)

( * ) Notice: Subject to any disclaimer, the term of this patent is extended or adjusted under 35 U.S.C. 154(b) by 203 days.

(21) Appl. No.: 10/270,789

(22) Filed: Oct. 11, 2002

(65) Prior Publication Data
US 2003/0096028 A1 May 22, 2003

Related U.S. Application Data

(62) Division of application No. 09/821,982, filed on Mar. 20, 2001, now abandoned.

(30) Foreign Application Priority Data

Aug. 7, 2000 (JP) ........................................ 2000-239064
Sep. 29, 2000 (JP) ........................................ 2000-299966

(51) Int. Cl.$^7$ .............................................. A61K 35/78
(52) U.S. Cl. ........................ 424/769; 424/725; 424/774; 424/776; 424/777; 424/779; 514/893
(58) Field of Search ................................ 424/769, 725, 424/774, 776, 777, 779; 514/893

(56) References Cited

U.S. PATENT DOCUMENTS

| | | | |
|---|---|---|---|
| 4,444,763 A | 4/1984 | Davis | |
| 4,560,568 A | 12/1985 | Curiel | |
| 5,514,709 A | 5/1996 | Counts et al. | |
| 6,057,366 A | 5/2000 | Seawright et al. | |

OTHER PUBLICATIONS

Werman, et al. Connective Tissue Res. 1991, vol. 26 (1–2) pp. 1–10 MEDLINE Abstract.
Werman, et al. Food Chem. Toxicol. 1991, vol. 29 (2), pp. 93–99.
Werman, et al. Food Chem. Toxicol. 1989 (vol. 27 (5), pp. 279–282.
Kamau, et al. Int. J. BioChemiPhysics. 1993 vol. 2 (1–2), pp. 81–84 CAPLUS Abstract.
Martinenghi, G. Brazil Ministerio Agr., Inst. Oleos Biol. 1958 No. 17, pp. 1–16 CAPLUS Abstract.
Martinez, et al. Grasas Aceites. 1988, vol. 39 (4–5), pp. 272–277 CAPLUS Abstract.
Kawagishi, et al., Tennen Yuki Kogobutsu Toronkal Koen Yoshishu 2000, 42$^{nd}$, pp. 517–522 CAPLUS Abstract.
Anupam Bishayee, et al., Hepatoprotective activity of carrot (*Daucus carota* L. against carbon tetrachloride intoxication in mouse liver, Journal of Ethnopharmacology 47 (1995) pp. 69–74.
Shizutoshi Nakagawa, et al., Cytoprotective Activity of Components of Garlic, Ginseng and Ciuwjia on Hepatocyte Injury Induced by Carbon tetrachloride in Vitro, Hiroshima Journal of Medical Sciences vol. 34, No. 3, pp. 303–309, Sep. 1985.
Kyoichi Kagawa, et al., Garlic Extract Inhibits the Enhanced Perioxidation and Production of Lipids in Carbon Tetrachloride–Induced Liver Injury Japan J. Pharmacol. 42, pp. 19–26, 1986.
Capatukob, A.C., et al. Khim.Farm. Zh., vol. 24, pp. 38–40 (1990), English summary.

*Primary Examiner*—Christopher R. Tate
(74) *Attorney, Agent, or Firm*—Knobbe, Martens, Olson & Bear, LLP

(57) ABSTRACT

A hepatic disorder suppressant comprising extracts having hepatic disorder suppressing effect as effective ingredients, wherein the extracts is obtained by extracting an avocado plant and/or a processed product thereof with an organic solvent is disclosed.

6 Claims, 4 Drawing Sheets

HEPATIC DISORDER SUPPRESSANT

This is a divisional of U.S. application Ser. No. 09/821,982, filed Mar. 30, 2001, now abandon which is incorporated herein by reference in its entirety.

FIELD OF THE INVENTION

The present invention relates to a hepatic disorder suppressant and novel compounds for use as effective ingredients of a hepatic disorder suppressant.

BACKGROUND OF THE INVENTION

Among hepatic disorders, studies related to acute hepatic disorders have progressed to some extent and various treatment have been done. However, since the cause of chronic hepatic disorders is unknown in many aspects, effective treatment for chronic hepatic disorders have not been established. The chronic hepatic disorders are thought to be the hepatic disorders caused by the failure of immune system.

For these chronic hepatic disorders, treatment by using Chinese herbal medicines have been done. In these Chinese herbal medicine treatment, Daisaikotou, Shousaikotou, Saikokeishitou, Saikokeikyoutou, Shigyakusan and the like are used ("Ippanyou Kanpou Shohou (Kanpou 210 shohou)", Nippon Seiyaku Dantai Rengoukai Kanpou Senmon Iinkai (1975), "Kanpou Gairon", Fujihira Ken and Ogura Shigenari, Sougensha (1979)). In respect of the effective ingredients of galenicals contained in these Chinese herbal medicines, many things are unknown. However, for example, it is known that Sanshichininjin has liver-protecting effect in its component (Japanese Patent Application No. Hei 8-46154). It is also known that these galenicals have a few side effects as their advantages.

However, it is difficult to obtain these galenicals because many of them are produced from the raw materials of overseas, and their effects are not always constant because wild plants may be used as the raw materials for these galenicals ("Shouyakugaku 4th ed.", Isao Kitagawa et al., Hirokawa Shoten, pp.384–387(1992)), ("Kanpouyaku no hyouka to kaihatsugijutsu", edited by Tokyo Shoyaku Kenkyuukai (CMC, Inc.) pp.353–354 (1983)). Since Chinese herbal medicines are generally expensive, it is difficult to use Chinese herbal medicine daily basis. Thus this is considered to be its disadvantage.

On the other hand, the efforts to extract effective ingredients having hepatic disorder suppressing effect, from vegetables has be done. Among vegetables, it has been known that garlic (Kagawa, K. et al. Japan. J. Pharmacol., Vol.42, pp.19–26 (1986), Nakagawa, S. et al. Hiroshima J. Med. Sci., Vol.34, pp.303–309 (1985)), carrot (Bishayee, A. et al. J. Ethnopharmacl., Vol.47, pp.69–74 (1995), and saltwort (CAPTИкOB, A.C. et al. Khim. Farm. Zh., Vol.24, pp.38–40 (1990)) have acute hepatic disorder suppressing effect, but vegetables having chronic hepatic disorder suppressing effect have not been known.

SUMMARY OF THE INVENTION

An object of the present invention is to provide a hepatic disorder suppressant, and an extract and compounds which can be used as an effective ingredient of a hepatic disorder suppressant.

To accomplish the above object, the present inventors have made intensive studies to find out that an extract extracted with a nonpolar organic solvent from avocado plant has excellent hepatic disorder suppressing effect. Furthermore, they have isolated and purified the compounds that exhibit hepatic disorder suppressing effect, and the structures of the compounds have been identified. They have also found out that novel compounds as well as known compounds are contained in the compounds showing hepatic disorder suppressing effect, then accomplished the present invention.

That is, the present invention is described below.

(1) A hepatic disorder suppressant comprising extracts having hepatic disorder suppressing effect as effective ingredients, wherein the extracts is obtained by extracting an avocado plant and/or a processed product thereof with an organic solvent.

(2) A hepatic disorder suppressant comprising, a substance having hepatic disorder suppressing effect, as an effective ingredient, wherein the substance is obtained by steps 1) extracting an avocado plant and/or a processed product thereof with an organic solvent, and
2) fractionating the extract by chromatography, wherein the substance has an Rf value between 0.19 and 0.25 when thin-layer chromatography is carried out on a Silica Gel 60 produced by Merck & Co., Inc. with an organic solvent of 4:1 n-hexane/ethyl acetate as the developing solvent.

(3) A hepatic disorder suppressant according to (1) or (2), wherein the organic solvent is a nonpolar organic solvent.

(4) A hepatic disorder suppressant according to (1) or (2), wherein the organic solvent is one or more selected from the group consisting of n-hexane, cyclohexane, benzene and carbon tetrachloride.

(5) A hepatic disorder suppressant according to (1) or (2), wherein the organic solvent is n-hexane.

(6) A hepatic disorder suppressant according to (2), wherein the chromatography is carried out by the use of a silica gel column.

(7) A pharmaceutical composition for suppressing hepatic disorders comprising a hepatic disorder suppressant according to (1) or (2).

(8) A food composition for suppressing hepatic disorders comprising a hepatic disorder suppressant according to (1) or (2).

(9) A linoleic acid derivative represented by the following formula (1).

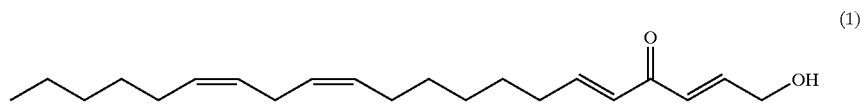

(1)

(10) A linoleic acid derivative represented by the following formula (2).

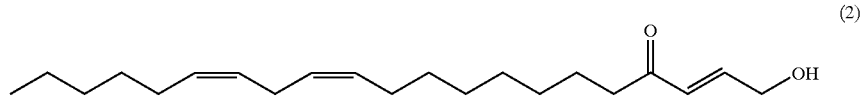

(2)

(11) An oleic acid derivative represented by the following formula (3).

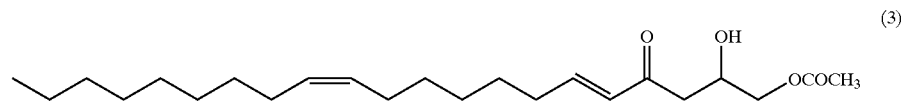

(12) A hepatic disorder suppressant comprising a compound according to (9) to (11), or a linoleic acid derivative represented by the following formula (4) or (5) as an effective ingredient.

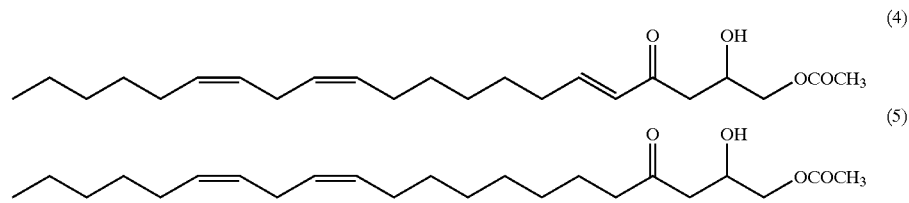

Since the novel unsaturated fatty acid derivatives of the present invention have excellent hepatic disorder suppressing effect, they can be used as the effective ingredients of a hepatic disorder suppressant. Moreover, the hepatic disorder suppressants comprising the unsaturated fatty acid derivatives of the present invention as effective ingredients, have excellent hepatic disorder suppressing effect, especially chronic hepatic disorder suppressing effect. Furthermore, the hepatic disorder suppressant of the present invention comprising an extract from an avocado plant as an effective ingredient has excellent hepatic disorder suppressing effect, especially chronic hepatic disorder suppressing effect. The hepatic disorder suppressant of the present invention is safe because it is derived from plant, and it can provide a pharmaceutical composition or food composition comprising the hepatic disorder suppressant which is easily prescribed, since it is easy to extract the hepatic disorder suppressant of the present invention.

DETAILED DESCRIPTION OF THE INVENTION

The present invention is further described in detail below. The present invention relates to a hepatic disorder suppressant, and extracts and compounds which can be used as effective ingredients of a hepatic disorder suppressant.
<1>The Hepatic Disorder Suppressant of the Present Invention The first hepatic disorder suppressant of the present invention is a hepatic disorder suppressant comprising extracts having hepatic disorder suppressing effect as effective ingredients, wherein the extracts is obtained by extracting an avocado plant and/or a processed product thereof with an organic solvent. The extracts having hepatic disorder suppressing effect comprise the extracts extracted with an organic solvent and the purified products thereof. Hereafter they are referred to as "substances having hepatic disorder suppressing effect" and explained.

The substances having hepatic disorder suppressing effect of the present invention are contained in sarcocarps, pericarps, seeds, leaves, leafstalks and branches of an avocado plant and the processed products thereof that are crushed, dried, or concentrated. Since the substances are contained especially in sarcocarps and pericarps, it is preferable to use these tissues and the processed products thereof.

The avocado plants used for the present invention belong to the genus *Persea* of the Laurel family. Alligator pear or *Persea* includes *P. americana,* Mexican race, Guatemalan race, Indian race and the like, especially *P. americana* is preferable. The extraction process of avocado plants is carried out by a conventional method such as the continuous method and batch-type method and so on, and by using cold or warm solvent for the desired period of time. For example, dry powder of an avocado plant is crushed, and dipped or shaken with an extracting solvent for 1 to 48 hours at room temperature. Then, the extraction residue is removed from the extracted solution, and the extract solution is concentrated by the filtration under reduced pressure or ultrafiltration. If necessary, the solvent is taken away by evaporation.

Among the solvents used for such an extraction process, organic solvents are preferable, and nonpolar organic solvents are more preferable. Specific examples of the solvents include n-hexane, cyclohexane, benzene and carbon tetrachloride. Of these solvents, n-hexane is preferable.

The extraction example of the substances having hepatic disorder suppressing effect of the present invention is illustrated below, but the present invention is not limited to these extraction examples. First, an avocado plant is freeze-dried, then to the dry powder thereof, n-hexane (not water-soluble and a nonpolar organic solvent) is added, thereby extracting the components soluble in this solvent. The amount of the solvent added to the avocado plant is preferably 1 to 200 ml per gram of the dry powder, more preferably 5 to 50 ml. Concerning extraction process, after this solvent is added to an avocado plant, the solution is stirred well with a stirrer and the like, thereby extracting the fractions soluble in a nonpolar organic solvent. This process is usually preferably repeated two times to 5 times. The solvent of the extraction fractions obtained in such a way is removed to obtain an oily extract. Concerning removing process of the solvent, various conventional methods can be applied such as evaporating away the solvent under atmospheric pressure or reduced pressure.

Furthermore, various chromatography methods such as adsorption chromatography and partition chromatography are used solely or combination with other methods to carry out chromatographic fractionation of the above extract, thereby further separating and purifying the extract. It is preferable to isolate and purify the unsaturated fatty acid derivatives represented by the formulae (1) to (5) to be contained in the hepatic disorder suppressant of the present invention from the fraction comprising the substances having hepatic disorder suppressing effect which is obtained by the above fractionation. The fractionated product comprising the substances having hepatic disorder suppressing effect (that is, the fraction comprising unsaturated fatty acid derivatives) is characterized by Rf value of between 0.19 and 0.25 when thin-layer chromatography (Silica Gel 60; Merck & Co., Inc., developing solvent; hexane/ethyl acetate=4/1) is carried out. Using this feature as an index, selection of fractionated products can be conducted.

The examples of chromatographic fractionation of the substances having hepatic disorder suppressing effect of the present invention are illustrated below, but the present invention is not limited to these examples.

The above-described extract is dissolved in solvent having low eluting ability, and the obtained eluent is subjected to fractionation by adsorption chromatography on a silica gel column. The elution is carried out step by step by adding solvents having high eluting ability with gradient. Then, the obtained eluents are fractionated by sampling periodically to separate and purify the extract. The fractionated extract comprising the substance having hepatic disorder suppressing effect can be obtained by removing the solvent from the fractions. Various conventional methods of removing the solvent such as evaporating the solvent under atmosphere pressure or reduced pressure can be used. Selection of the fractionated extract can be performed according to the above-mentioned method.

Well-Known methods for testing hepatic disorder effect can be used to determine whether the above-mentioned extracts and fractionated extracts comprise the substances having hepatic disorder suppressing effect or not. For example, models animals such as mouse and the like are divided into two groups.

While the extracts or the fractionated extract are administered for a certain period of time to the model animals of one group, nothing is administered to the model animals of the other group. After substances inducing hepatic disorders such as D-galactosamine are administered to them of each group, enzyme activities such as ALT and AST in model animals of each group are measured. The obtained data is used as an index of hepatic disorder to determine whether the extracts have hepatic disorder suppressing effect or not. Thus, it can be determined whether the extracts comprise the substances having hepatic disorder suppressing effect or not.

Next, the second hepatic disorder suppressant of the present invention is explained. The second hepatic disorder suppressant of the present invention comprises the compounds represented by the formulae (1) to (5) as effective ingredients. The compounds used as effective ingredients of the hepatic disorder suppressant of the present invention encompass novel linoleic acid derivatives represented by the formula (1) or (2), a novel oleic acid derivative represented by the formula (3), and linoleic acid derivatives represented by the formula (4) or (5). Hereafter the compounds represented by the formulae (1) to (3) are referred to "novel unsaturated fatty acid derivatives", and compounds represented by the formulae (1) to (5) are referred to "unsaturated fatty acid derivatives" and explained hereinafter.

First, novel unsaturated fatty acid derivatives used as effective ingredients of a hepatic disorder suppressant are described. The novel unsaturated derivatives of the present invention are the compounds having the structures of the above-described formula (1) to (3). That is, Compound 1 represented by the formula (1) (molecular weight 318: $C_{21}H_{34}O_2$) is (2E, 5E, 12Z, 15Z)-1-hydroxyhenicosa-2, 5, 12, 15-tetraen-4-one. Compound 2 represented by the formula (2) (molecular weight 320: $C_{21}H_{36}O_2$) is (2E, 12Z, 15Z)-1-hydroxyhenicosa-2, 12, 15-trien-4-one. Compound 3 represented by the formula (3) (molecular weight 380: $C_{23}H_{40}O_4$) is (5E, 12Z)-1(acetyloxy)-2-hydroxyhenicosa-5, 12-dien-4-one. The unsaturated fatty acid derivatives of the formula (1) to (3) are novel compounds that are first isolated, purified and identified in the present invention, and have excellent hepatic disorder suppressing effect, especially chronic hepatic disorder suppressing effect.

The unsaturated fatty acid derivatives represented by the formula (4) and (5) are known compounds that are isolated from an avocado, and together with the above compounds represented by the formula (1) to (3), they were isolated and purified as compounds showing hepatic disorder suppressing effect.

It has been reported that Compound 4 of the formula (4) has inhibitory effect on NO and $O_2^-$ generation (BIO INDUSTRY, Vol.15, No.8, pp.34–40 (1998)). Compound 5 of the formula (5) is called "persin", and is observed to have various growth suppressing effect as well as inhibitory effect on NO and $O_2^-$ generation, and its physiological effect has been studied (Journal of Natural Products, Vol.61, No.9, pp.1168–1170 (1998), Natural Toxins, 3, pp.344–349 (1995), BIO INDUSTRY, Vol.15, No.8, pp.34–40 (1998), WO 95/22696). However, hepatic disorder suppressing effect of the compounds of formula (4) and (5) has not yet been reported. It has been proved for the first time in the present invention that these compounds have excellent hepatic disorder suppressing effect, especially chronic hepatic disorder suppressing action.

Thus, all of the unsaturated fatty acid derivatives represented by the formulae (1) to (5) have hepatic disorder suppressing effect, and are colorless and oily compounds at room temperature having molecular weights of 300 to 400. Since these compounds can be dissolved in various solvents such as hexane and ethyl acetate, for example, they can be used by being mixed properly with fat-soluble substances such as various fatty acids which is liquid at room temperature.

The unsaturated fatty acid derivatives of the above-described formula (1) to (5) can be obtained by solvent extracting from an avocado plant, separating and purifying by the following method, or can be obtained by chemical synthesis.

In respect of chemical synthesis methods, the unsaturated fatty acid derivatives of the present invention can be synthesized by aldol condensation of aldehyde derivatives and methyl ketone (Paterson I, Goodman J M, Lister M A, Schumann R C, McClure C K, Norcross R D, Tetrahedron 46, pp.4663–4684 (1990)), for example, as described in Natural Toxins, 3, pp.344–349 (1995). These derivatives can also be synthesized in combination with known methods properly. These derivatives can be synthesized by the method described in International Publication WO95/22969 or the modified method thereof.

The unsaturated fatty acid derivatives of the formula (1) to (5) having hepatic disorder suppressing effect of the present invention can be obtained, for example, by extracting from an avocado plant with an organic solvent, isolating and purifying as described above.

The fractionated extracts comprising hepatic disorder suppressing effect is further fractionated by high performance liquid chromatography (HPLC), for example under the condition that the composition of eluents is properly adjusted, to obtain the novel compounds 1 to 3 of the present invention and compounds 4 and 5 having hepatic disorder suppressing effect. Identification of the compounds isolated and purified by the fractionation can be performed by using the observed data obtained by conventional methods such as $^1$H-NMR, $^{13}$C-NMR, IR spectrum and UV spectrum.

When the hepatic disorder suppressant of the present invention comprises the compounds of the above-described formula (1) to (5) as effective ingredients for suppressing hepatic disorders, these compounds of the formula (1) to (5) can be used solely, or in combination of two compounds or more.

<2> The Pharmaceutical Composition for Suppressing Hepatic Disorders Comprising a Hepatic Disorder Suppressant of the Present Invention The pharmaceutical composition of the present invention is a composition that comprises the above-described hepatic disorder suppressant, produced by conventional methods, and it is not particularly limited as long as it is expected to have hepatic disorder suppressing effect.

Dosage form of the pharmaceutical composition of the present invention is not particularly limited, however, such as tablet, granule, capsule, julep, drink and the like is preferable under the condition that the hepatic disorder suppressant is mixed with one or more kinds of carrier, excipient, integrator, preservative, stabilizer, flavor and the like as long as generally permitted for preparation. Such a preparation can be carried out by conventional methods used for usual production of pharmaceutical composition. The dosage of the above-described pharmaceutical composition varies depends on kinds of diseases, symptoms, ages of patients, weights of patients and the like, in case of adult, it is preferable to administer, orally, 1 to 100 mg of the unsaturated fatty acid derivatives of the formula (1) to (5) per day at once or at several times. It is also preferable to administer, orally, 100 to 1000 mg of the extract of an avocado plant with a nonpolar organic solvent at once or at several times, and 10 to 500 mg of fractionated extract obtained by chromatographic fractionation at once or at several times.

<3> The Food Composition for Suppressing Hepatic Disorders Comprising a Hepatic Disorder Suppressant of the Present Invention The food composition of the present invention is a composition that comprises the above-described hepatic disorder suppressant, produced by conventional methods. The food composition of the present invention is not particularly limited as long as it comprises the above-described hepatic disorder suppressant. The extract comprising hepatic disorder suppressant can be mixed with food materials together with various optional components, which are conventionally used as foods for desired amount. When the extract is added, particular attention needs not to be paid. Health foods and functional foods can be produced by conventional processing methods. The amounts of the extract depend on the kinds of foods. It is preferable to add 0.001 to 1% by weight of the unsaturated fatty acid derivatives of the formulae (1) to (5), and 0.01 to 10% by weight of the above-described extract or fractionated product, against whole weight of the foods in order not to change the taste of the foods and but to achieve enough hepatic disorder suppressing effect.

EXAMPLES

The present invention is illustrated in further detail by the following examples.

Example 1

<Extraction of the Effective Ingredients of the Present Invention>

Figure 1:
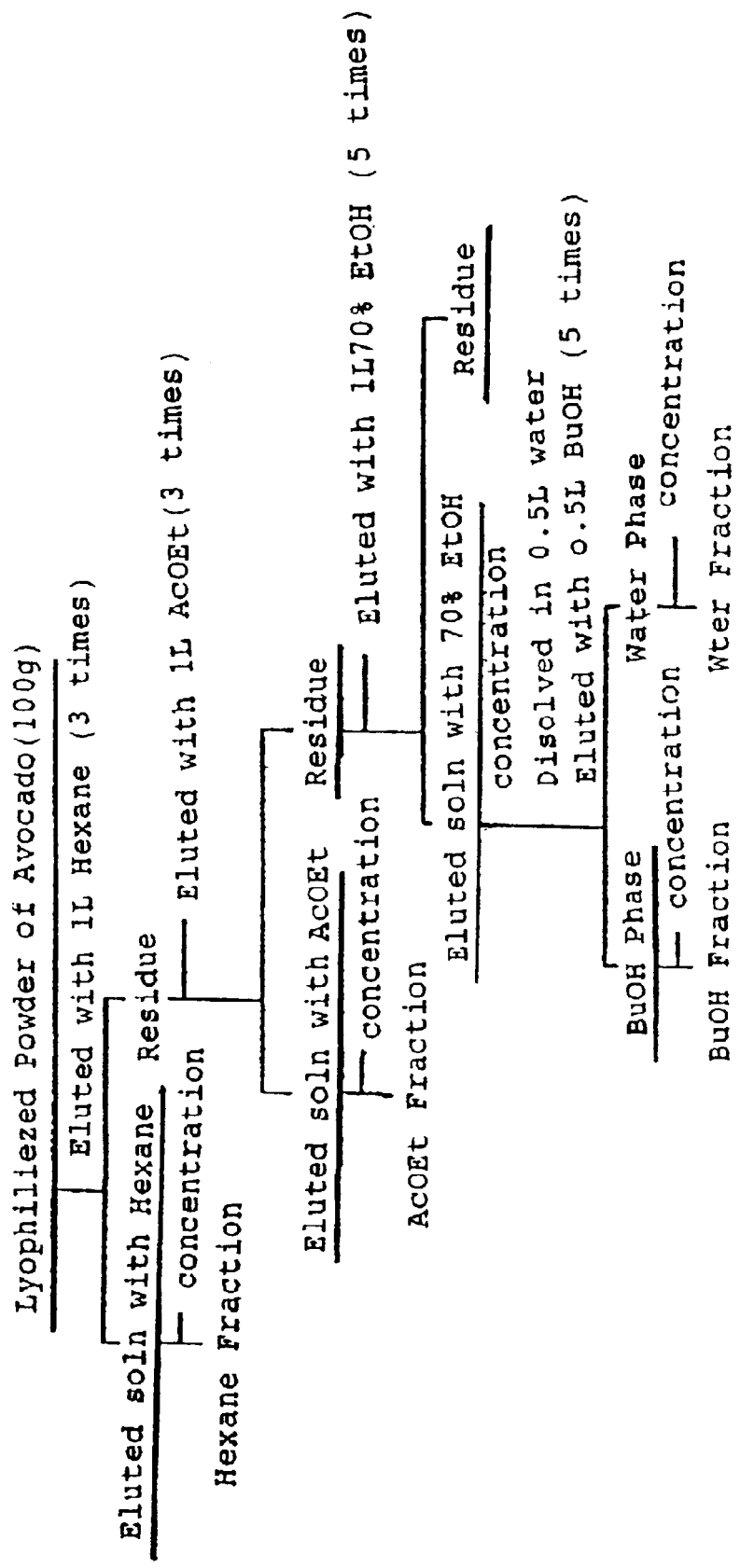
FIG. 1 is one illustration to extract effective ingredients of the hepatic disorder suppressant from an avocado.

A sarcocarp of an avocado was freeze-dried to obtain a dry powder. This dry powder was fractionated by following the scheme shown in FIG. 1 to use for the following evaluation.

(a) Fractionation with Hexane

To 100 g of dry powder obtained by freeze-drying a sarcocarp of an avocado, 1 liter of n-hexane was added and stirred sufficiently, then the residues were removed to obtain a supernatant as hexane extract. This treatment was repeated further two times, and 3000 ml of hexane extract solution was obtained by the three times' treatment in total. This extract solution was concentrated by using an evaporator to obtain 58.6 g of an oily concentrated product from hexane fraction.

(b) Fractionation with Ethyl Acetate

Next, to 41.4 g of the residues of the above treatment (a), 1 liter of ethyl acetate was added and stirred sufficiently, then the residues were removed to obtain a supernatant as ethyl acetate extract. This treatment was repeated further two times, and 3000 ml of ethyl acetate extract was obtained by the three times' treatment in total. This extract solution was concentrated and dried by using an evaporator to obtain 0.8 g of a solid product from ethyl acetate fraction.

(c) Fractionation with 70% Ethanol

Next, to 40.6 g of the residues of the above treatment (b), 1 liter of 70% ethanol was added and stirred sufficiently, then the residues were removed to obtain a supernatant as 70% ethanol extract. This treatment was repeated further four times, and 5000 ml of 70% ethanol extract was obtained by the five times' treatment in total. This extract solution was concentrated and dried by using an evaporator to obtain 16.0 g of a solid product from 70% ethanol fraction. By the treatment (c), 24.6 g of ethanol residue was also obtained.

(d) Fractionation with Butyl Alcohol (Butanol)

Next, 16.0 g of concentrated dried product obtained by the above treatment (c) was dissolved to 500 ml of distilled water. Then, to this solution, 500 ml of n-butanol was added and stirred sufficiently, then the butanol layer was extracted by countercurrent distribution by using a separatory funnel. To the remained water layer, 500 ml of n-butyl alcohol was further added and stirred sufficiently, then the extraction by n-butyl alcohol was carried out. This extraction was repeated further three times, 2500 ml of butyl alcohol extract was obtained by the five times' extraction treatment in total. This butyl alcohol extract solution was concentrated and dried by using an evaporator to obtain 2.8 g of a solid product was obtained from butyl alcohol fraction.

In the treatment (d), the solution of the water layer was concentrated and dried by using a freeze-drying apparatus to obtain 13.2 g of a solid product from water-soluble fraction.

Partition ratio (% by weight) to each fraction obtained by the above-described fractionating treatment is shown in Table 1. Here, partition ratio is a value that weight of a solid product obtained from each fraction is divided by the weight before fractionation (100 g), and further multiplied by 100 for percentage.

TABLE 1

Partition ratio to each fraction

|  | Partition ratio |
| --- | --- |
| Hexane fraction | 58.6% |
| Ethyl acetate fraction | 0.8% |
| Butanol fraction | 2.8% |
| Water-soluble fraction | 13.2% |
| Ethanol extraction residue | 24.6% |

(e) Fractionation of Hexane Fraction on a Silica Gel Column

The similar treatment to the treatment (a) was carried out again on a large scale to obtain an oily concentrated product of hexane fraction. Thus obtained 100 g of a oily concentrated product was dissolved again in 500 ml of hexane/ethyl acetate mixture (5/1). This solution was applied on a silica gel column (Silica Gel 60; Merck & Co., Inc., 8×73 cm), and elution was carried out with solvents with different composition. The solvents used in this elution are hexane/ethyl acetate (5/1), hexane/ethyl acetate (4/1), hexane/ethyl acetate (3/2), hexane/ethyl acetate (2/3), ethyl acetate and methanol. These solvents were applied into the column in the above-described order, eluent solution were taken out periodically to obtain extracts. These extracts were subjected to thin-layer chromatography (Silica Gel 60; Merck & Co., Inc., developing solvent; hexane/ethyl acetate=4/1), and when the band having UV absorption cannot be detected, an elution solvent was changed to the next solvent. Fractions of these eluent solution were subjected to thin-layer chromatography (Silica Gel 60; Merck & Co., Inc., developing solvent; hexane/ethyl acetate=4/1), the obtained Rf values were used as index, thereby fractionating to seven fractions. Yield of each fraction was as follows: fraction 1, 84.1 g; fraction 2, 1.2 g; fraction 3, 1.8 g; fraction 4, 7.1 g; fraction 5, 1.9 g; fraction 6, 1.5 g; fraction 7, 2.4 g. Rf value in thin-layer chromatography, partition ratio, and composition of elution solvent for each fraction are shown in Table 2.

TABLE 2

Rf value, partition ratio, composition of elution solvent for each fraction

|  | Rf value | Partition ratio (%) | Elution solvent |
| --- | --- | --- | --- |
| Fraction 1 | 0.76 | 84.1 | Hexane/ethyl acetate = 5/1 |
| Fraction 2 | 0.54 | 1.2 | Hexane/ethyl acetate = 4/1 |
| Fraction 3 | 0.40 | 1.8 | Hexane/ethyl acetate = 4/1 |
| Fraction 4 | 0.22 | 7.1 | Hexane/ethyl acetate = 3/2 |
| Fraction 5 | 0.10 | 1.9 | Hexane/ethyl acetate = 2/3 |
| Fraction 6 | 0.05 | 1.5 | Ethyl acetate |
| Fraction 7 | 0.00 | 2.4 | Methanol |

Example 2

Then, after the above fractionations, fraction 4 was dissolved again to 98:2 acetonitrile/water mixture solvent, and was subjected to high performance liquid chromatography (acetonitrile:water=98:2, UV/VIS detector: 220 nm) using ODS column (Wakosil-II 5C18HG Prep, Wako Pure Chemical Industries, Ltd.) to obtain five compounds. Yields of these compounds are shown in Table 3 below.

TABLE 3

Yields of each compound

|  | Yield (%) |
| --- | --- |
| Compound 1 | 18.8 |
| Compound 2 | 35.1 |
| Compound 3 | 2.1 |
| Compound 4 | 18.8 |
| Compound 5 | 7.2 |

Here, the yield stands for a value that the weight of each compound obtained is divided by the weight before fractionation (weight subjected to ODS column: 10.45 g), and further multiplied by 100 for percentage. Identification of above-described compounds 1 to 5 was carried out to obtain the following results.

(1) Compound 1
1. Molecular Weight 318 ($C_{21}H_{34}O_2$)
2. Infrared Absorption Spectrum: 3420, 1740, 1667, 1616 $cm^{-1}$
3. Chemical shift by $^1$H-NMR (δ): 0.87(3H, t, J=6.9), 1.27(4H, m), 1.34(6H, m), 1.47(2H, m), 2.05(4H, m), 2.23 (2H, dt, J=7.0, 6.4), 2.75(2H, dd, J=6.1, 6.1), 4.38(2H, br, s), 5.30(2H, m), 5.34(2H, m), 6.29(1H, dt, J=14.3, 1.2), 6.62 (1H, dt, J=15.4, 2.1), 6.91(1H, m), 6.93(1H, m)
4. Chemical shift by $^{13}$C-NMR (δ): 14.0, 22.5, 25.6, 27.1, 27.2, 28.0, 28.8, 29.3, 29.4, 31.5, 32.7, 62.2, 126.3, 127.8, 128.3, 129.2, 129.8, 130.3, 144.8, 148.7, 189.2
5. Color and Property: colorless and oily According to the above analytical results, Compound 1 was identified as a novel linoleic acid derivative having the following formula (1).

(2) Compound 2
1. Molecular Weight 320 ($C_{21}H_{36}O_2$)
2. Infrared Absorption Spectrum: 3430, 1668 $cm^{-1}$
3. Chemical shift by $^1$H-NMR (δ): 0.86(3H, t, J=6.8), 1.27(14H, m), 1.57(2H, m), 2.02(4H, m), 2.51(2H, t, J=7.5), 2.78(2H, t, J=6.6), 4.3(2H, m), 5.32(4H, m), 6.33(1H, ddd, J=15.9, 3.1, 2.1), 6.85(1H, dt, J=15.9, 4.0)
4. Chemical shift by $^{13}$C-NMR (δ): 13.9, 22.4, 24.0, 25.5, 27.0, 29.0, 29.1, 29.2, 29.5, 31.4, 40.0, 61.6, 127.76, 127.84, 127.9, 129.8, 130.0, 145.1, 201.0, 189.2
5. Color and Property: colorless and oily According to the above analytical results, Compound 2 was identified as a novel linoleic acid derivative having the following formula (2).

(3) Compound 3
1. Molecular Weight 380 ($C_{23}H_{40}O_4$)
2. Infrared Absorption Spectrum: 3454, 1741, 1667 $cm^{-1}$
3. Chemical shift by $^1$H-NMR (δ): 0.84(3H, t, J=6.9), 1.22(16H, m), 1.43(2H, m), 2.00(4H, m), 2.06(3H, s), 2.19 (2H, m), 2.73(2H, d, J=6.1), 4.05(1H, dd, J=11.3, 6.1), 4.10(1H, dd, J=11.3, 4.1), 4.30(1H, ddt, J=4.1, 6.1, 6.1), 5.31(2H, m), 6.07(1H, d, J=15.9), 6.85(1H, dt, J=15.9, 7.0)
4. Chemical shift by $^{13}$C-NMR (δ): 14.0, 22.6, 27.1, 27.9, 29.1, 29.28, 29.31, 29.4, 29.56, 29.58, 29.6, 31.9, 32.5, 42.3, 66.1, 67.3, 130.2, 149.5, 171.0, 199.6
5. Color and Property: colorless and oily According to the above analytical results, Compound 3 was identified as a novel oleic acid derivative having the following formula (3).

(4) Compound 4
Compound 4 was identified by IR and NMR in the same manner as Compounds 1 to 3, and was confirmed as a linoleic acid derivative having the following formula (4) (molecular weight 378 ($C_{23}H_{38}O_4$), colorless and oily substance, described in Bio Industry, 15, 8. pp.34–40 (1998)).

(5) Compound 5

Compound 5 was identified by IR and NMR in the same manner as Compounds 1 to 3, and was confirmed as a linoleic acid derivative having the following formula (5) (molecular weight 380 ($C_{23}H_{40}O_4$), colorless and oily substance, described in Natural Toxins, 3, pp.344–349 (1995)).

Then, the above fractions 1 to 7 and Compounds 1 to 5 were evaluated for their liver-protecting effect against chronic hepatitis by using a hepatic disorder rat model induced by D-galactosamine.

<Evaluation of Hepatic Disorder Suppressing Effect>

The hepatic disorder model induced by carbon tetrachloride is an acute toxic hepatic disorder model. On the other hand, the hepatic disorder model induced by D-galactosamine is a chronic hepatitis model, which suggests the latter model is the hepatic disorder model related to the failure of immune system. The correlation between the latter model and the results of clinical testing were high.

Example 3

<Evaluation of Hepatic Disorder Suppressing Effect of Fractions 1 to 7>

Five week-old male Wistar rats were used for evaluation. After kept for 4 to 5 days, test rats were divided into groups under the condition that the average weight of each group was nearly the same and each group has 7 rats. The test feed were provided for each group respectively, for two weeks. Throughout the test period, the amount of feed taken and body weight were measured everyday.

Feed composition used in the test is shown in Table 4. Each fraction obtained by Example 1 was used as a test additive, and the amount of a test additive is shown in Tables 5 and 6. The amount of each composition in Table 4 is shown as gram per kg of the feed. The test additive and cornstarch in Table 4 indicates that the total of the amount of test additive described in Tables 5 or 6, and the amount of cornstarch is 401 g/kg. The feed of the control does not contain any test additive and contains 401 g/kg of cornstarch.

The amounts of the test additives in Table 5 were equivalent to 5% by weight addition of avocado sarcocarp dry powder respectively, and the amounts of the additives in Table 6 were equivalent to 3.8% by weight addition of the hexane fraction respectively.

TABLE 4

Feed composition

| Composition | Amount (g/kg) |
|---|---|
| Casein | 250 |
| Test additive and cornstarch | 401 |
| Sucrose | 200 |
| Corn oil | 50 |
| Mineral mixture[1] | 35 |
| Vitamin mixture[1] | 10 |
| Choline bitartrate | 4 |
| Cellulose | 50 |

Note)
[1]AIN-76 composition

TABLE 5

Test additive from each fraction

| Fraction | Added amount (g/kg) |
|---|---|
| Hexane fraction | 29.3 |
| Ethyl acetate fraction | 0.4 |
| Butanol fraction | 1.4 |
| Water-soluble fraction | 6.5 |
| Ethanol extraction residue | 12.3 |

TABLE 6

Test additive from each fraction

| Fraction | Added amount (g/kg) |
|---|---|
| Fraction 1 | 31.96 |
| Fraction 2 | 0.46 |
| Fraction 3 | 0.68 |
| Fraction 4 | 2.70 |
| Fraction 5 | 0.72 |
| Fraction 6 | 0.57 |
| Fraction 7 | 0.91 |

After the test rats are raised with the above-described test feed for 2 weeks, 350 mg/kg of D-galactosamine that induces hepatic disorders was administered into peritoneum thereof. Then, 22 hours after the administration, the test rats were killed and their blood was sampled and their livers were taken out.

In the sample blood, the activity of enzymes, whose concentration is known to increase in blood in accordance with failure of hepatocytes, that is alanine aminotransferase (ALT) activity and aspartate aminotransferase (AST) activity, were measured by using a commercially available measuring kit (Wako Pure Chemical Industries, Ltd.).

The increase and decrease of these enzyme activities was used as an index of hepatic disorders. The results are shown in FIG. 2 and FIG. 3.

Figure 2:
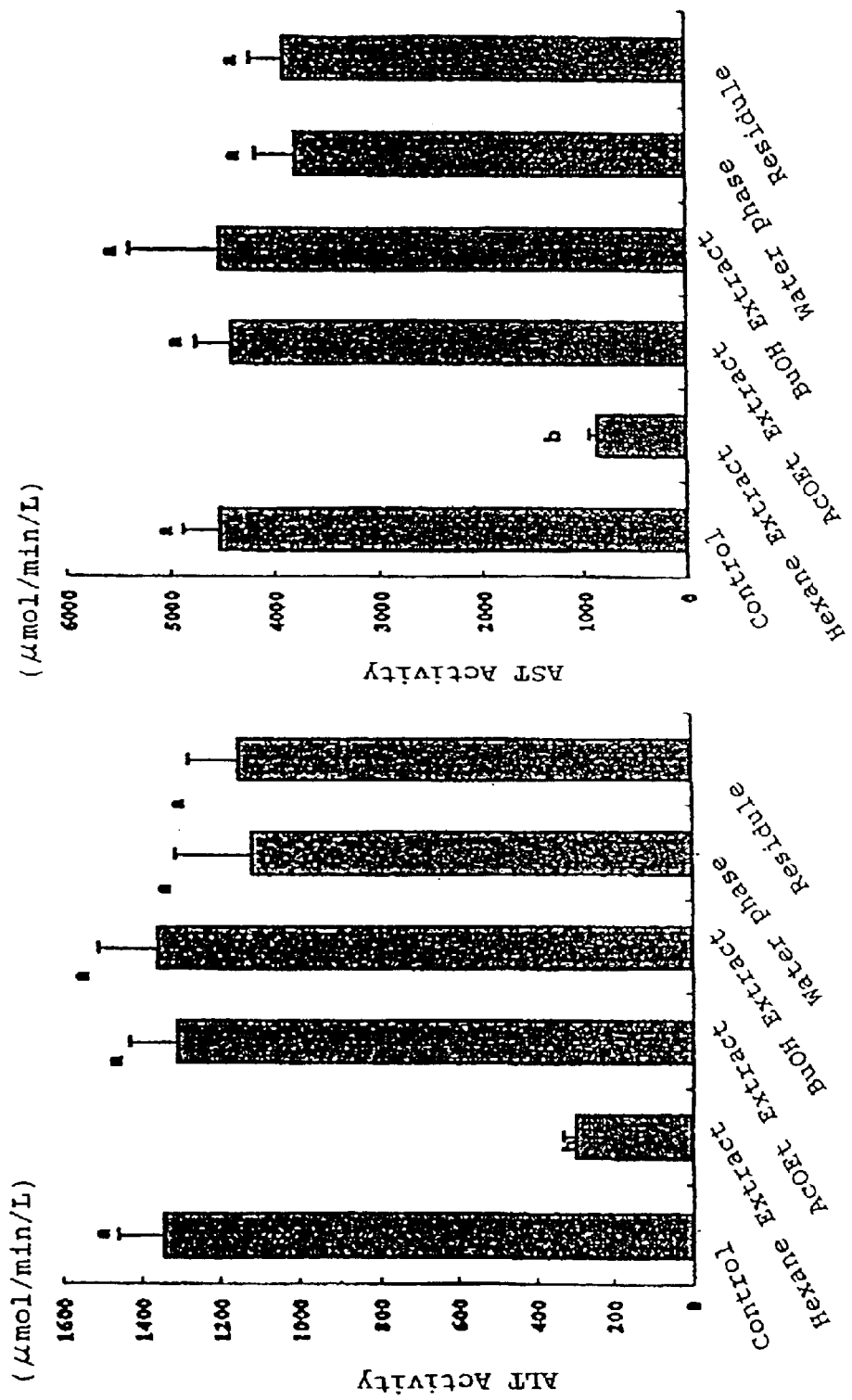
FIG. 2 shows values of ALT and AST activity at 22 hours after the administration of chemical substance for the groups given each fractionation which was extracted with solvent from an avocado.
Figure 3:
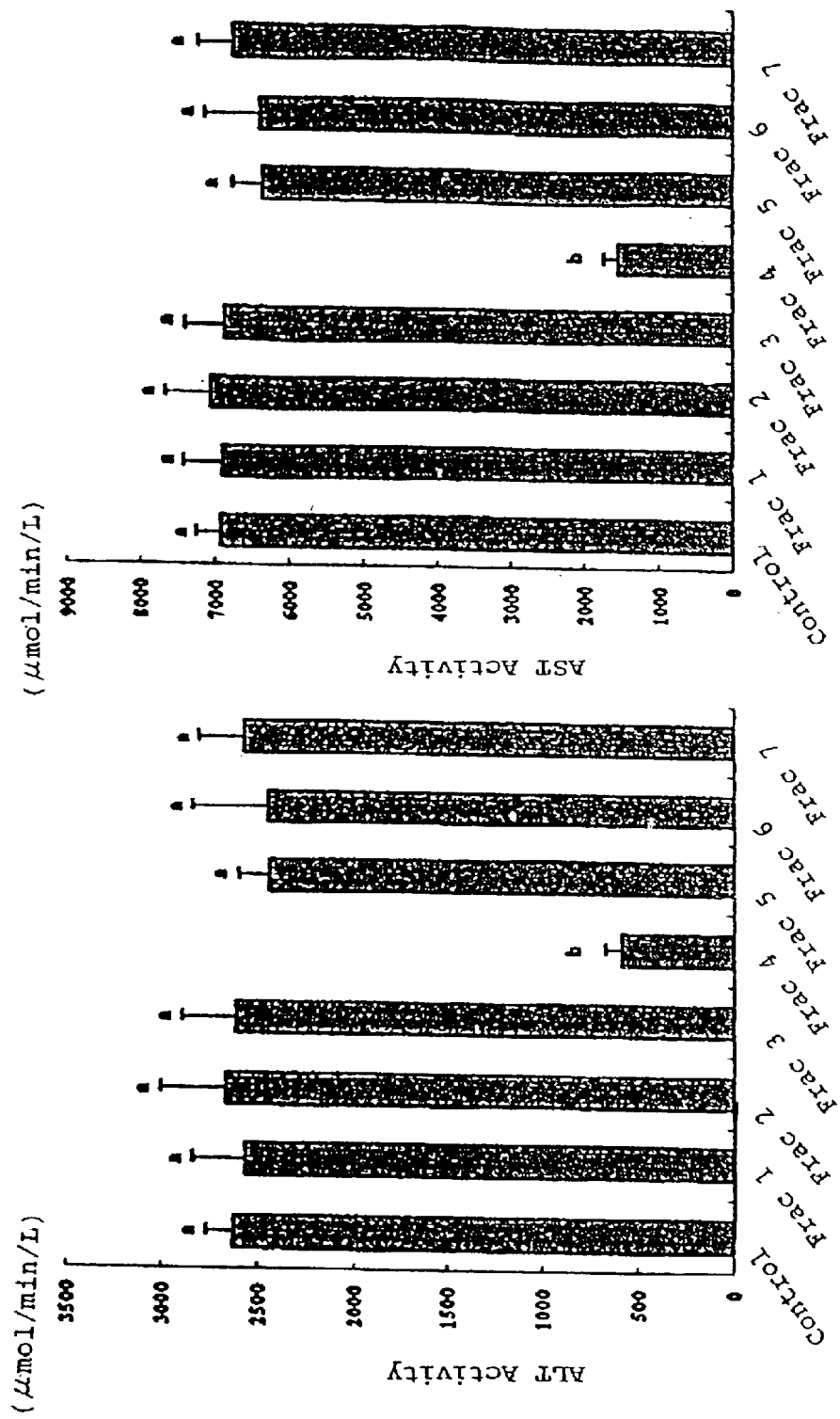
FIG. 3 shows values of ALT and AST activity at 22 hours after the administration of chemical substance for the groups given each fractionation which was extracted by chromatography from an avocado.

As shown in FIG. 2, the control group of rats showed rapid increase of both enzymes activities, and this suggests necrosis of hepatocytes. On the other hand, in the group of the rats raised with feeds including the test additive from each fraction of avocado solvent extract, hepatic disorder suppressing effect was obviously observed for the group of the rats raised with feeds including the hexane fraction.

Alphabets (a, b) shown in FIG. 2 indicate that there are significant differences between group having same alphabets and group having different alphabets statistically, at less than 5% of level of significance (after analysis of variance, a test is carried out by Duncan method as a post statistical test method).

The increase of body weight and the amount of feed taken during 3 days' test feeding, and liver weight per 100 g of body weight after 3 days' test feeding, are shown in Table 7. When the hexane fraction, which is confirmed to have hepatic disorder suppressing effect, was added as one of the feed and the group of rat was raised with the feed, the amount of feed taken and the increase of body weight of the group are significantly less than those of the other groups. It was also observed that the decrease of body weight was due to the decrease of feed taken during 3 days' test period. This proves that the hexane fraction has suppressing effect of feed uptake. The liver weight of the group of rats raised with the feed including hexane fraction was significantly heavier than that of the control group. This suggests that the addition of the hexane fraction suppressed the failure of hepatocytes due to necrosis.

TABLE 7

Body weight increase and feed uptake during testing

| Feed Control | Body weight (g/3d) | Feed uptake (g/3d) | Liver weight (g/Body weight 100 g) |
|---|---|---|---|
| (+ galactosamine treatment) | 9.3 ± 0.5 | 34.8 ± 0.5 | 3.56 ± 0.08 |
| + Hexane fraction | −9.9 ± 1.5 | 13.6 ± 1.6 | 3.82 ± 0.10 |
| + Ethyl acetate fraction | 10.0 ± 1.0 | 35.0 ± 1.0 | 3.62 ± 0.10 |
| + Butanol fraction | 10.6 ± 0.5 | 35.1 ± 1.1 | 3.64 ± 0.12 |
| + Water-soluble fraction | 10.6 ± 1.1 | 36.4 ± 1.0 | 3.65 ± 0.08 |
| + Ethanol extraction residue | 10.1 ± 0.9 | 35.5 ± 1.1 | 3.63 ± 0.09 |

As shown in FIG. 3, in the control group of rats showed rapid increase of both enzymes activities, and this suggests necrosis of hepatocytes. On the other hand, in the group of the rats raised with feeds including the test additive from each fraction of avocado solvent extract, hepatic disorder suppressing effect was obviously observed for the group of the rats raised with feeds including the fraction 4 obtained by further fractionating hexane fraction.

Alphabets (a, b) shown in FIG. 3 indicate that there are significant differences between group having same alphabets and group having different alphabets statistically, at less than 5% of level of significance (after analysis of variance, a test is carried out by Duncan method as a post statistical test method).

The increase of body weight and the amount of feed taken during 3 days' test feeding, and liver weight per 100 g of body weight after 3 days' test feeding, are shown in Table 8. When the fraction 4, which is confirmed to have hepatic disorder suppressing effect, was added as one of the feed and the group of rat was raised with the feed, the amount of feed taken and the increase of body weight of the group are significantly less than those of the other groups. It was also observed that the decrease of body weight was due to the decrease of feed taken during 3 days' test period. This proves that the fraction 4 has suppressing effect of feed uptake. The liver weight of the group of rats raised with the feed including fraction 4 was significantly heavier than that of the control group. This suggests that the addition of the fraction 4 suppressed the failure of hepatocytes due to necrosis.

TABLE 8

Body weight increase and feed uptake during testing

| Feed Control | Body weight increase (g/3d) | Feed uptake (g/3d) | Liver weight (g/Body weight 100 g) |
|---|---|---|---|
| (+ galactosamine treatment) | 10.6 ± 0.7 | 40.7 ± 1.2 | 3.69 ± 0.09 |
| + Fraction 1 | 12.8 ± 0.6 | 41.3 ± 0.9 | 3.64 ± 0.06 |
| + Fraction 2 | 10.9 ± 0.7 | 40.7 ± 1.3 | 3.65 ± 0.07 |
| + Fraction 3 | 10.5 ± 0.8 | 40.1 ± 1.2 | 3.68 ± 0.08 |
| + Fraction 4 | −1.8 ± 1.7 | 22.6 ± 1.4 | 3.99 ± 0.06 |
| + Fraction 5 | 9.7 ± 0.7 | 38.7 ± 1.1 | 3.63 ± 0.05 |
| + Fraction 6 | 10.2 ± 1.0 | 38.5 ± 1.1 | 3.65 ± 0.08 |
| + Fraction 7 | 9.0 ± 0.6 | 38.7 ± 1.1 | 3.56 ± 0.05 |

Example 4
<Comparison with Other Plants Having Hepatic Disorder Suppressing Effect>

Saltwort, carrot and garlic, which has been reported to have suppressing effect for hepatic disorders induced by carbon tetrachloride, were tested for their suppressing effects compared with avocado. The freeze-dried powder of eatable portion of each plant was used as a test additive.

Liver-protecting effect against chronic hepatitis was evaluated by a hepatic disorder model induced by D-galactosamine, with seven rats for each group. Composition of the feed used in the experiment is according to Table 4. 30 g/kg of each plant dry powder was added to the feed as a test additive. The content of the powder and cornstarch was 401 g/kg (powder 30 g/kg+cornstarch 371 g/kg). In the control group, no test additive was added, and 401 g/kg of cornstarch was used.

The enzyme activities were measured in the same manner as in Example 3, and the results are shown in Table 9. The values of the respective groups in Table 9 show the relative values under the condition that the value of the control group is regarded as 100, and are represented by average±standard deviation.

TABLE 9

Comparison with materials having suppressing action against hepatic disorders induced by carbon tetrachloride

|  | ALT | AST |
|---|---|---|
| Control | 100 | 100 |
| Avocado (3% by weight added) | 22.5 ± 1.6 | 17.5 ± 0.8 |
| Saltwort (3% by weight added) | 74.9 ± 8.2 | 82.1 ± 8.9 |
| Carrot (3% by weight added) | 89.6 ± 4.9 | 87.8 ± 5.4 |
| Garlic (3% by weight added) | 57.4 ± 5.5 | 51.4 ± 7.1 |

If saltwort and carrot are added at the same amount as avocado, no significant liver-protecting effect was observed. In comparison with the control group, the group that garlic was added suppressed significantly hepatic disorders induced by D-galactosamine, but the degree of suppression was lower than the group that avocado was added.

Example 5
<Evaluation of Hepatic Disorder Suppressing Effect of Compounds 1 to 5>

Six week-old male Wistar rats were used for evaluation. After kept for 10 days, test rats were divided into groups under the condition that the average weight of each group was nearly the same and each group has 7 rats. The above respective compounds 1 to 5 were dissolved in avocado oil (obtained by extracting avocado sarcocarp with hexane, applying the extract to silica gel chromatography, and collecting triglyceride fraction) (concentration: 100 mg/0.3 ml), the solution was injected into stomach of a rat using a catheter so that the amount of each compound was 100 mg per kg of weight of a rat.

In the placebo treatment group and the control group, only avocado oil was injected into stomach of a rat using a catheter.

Four hours after the administration of the above compounds, D-galactosamine, which induces hepatic disorders, was administered into the peritoneum of rats so that the amount was 350 mg per kg of weight of a rat. Then, 22 hours later, blood of a rat was sampled. In the placebo treatment group, after physiological saline was administered into the peritoneum of rats, blood was sampled in the same condition.

Next, in the sample blood, the activity of enzymes, whose concentration is known to increase in blood in accordance with failure of hepatocytes, that is alanine aminotransferase (ALT) activity and aspartate aminotransferase (AST) activity, were measured by using a commercially available measuring kit (Wako Pure Chemical Industries, Ltd.). The increase and decrease of these enzyme activities was used as an index of hepatic disorders. The results are shown in FIG. 4.

Figure 4:
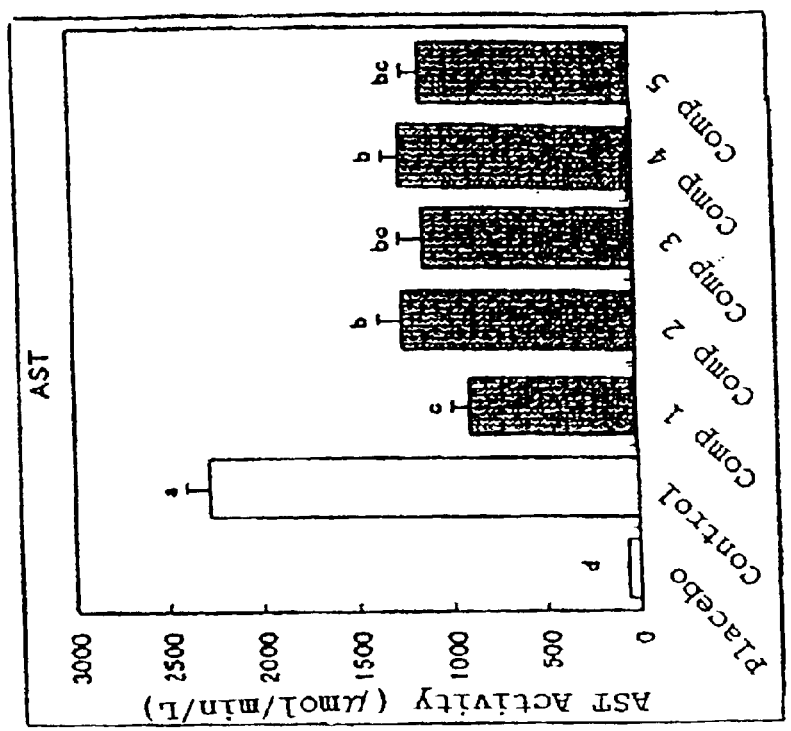
FIG. 4 shows values of ALT and AST activity at 22 hours after the administration of chemical substance.
Figure 4:
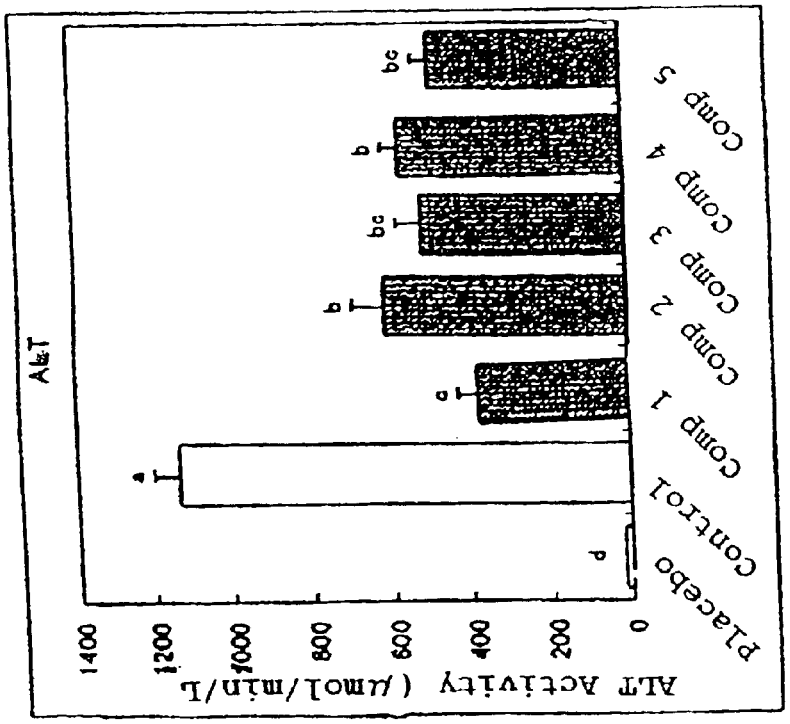

As shown in FIG. 4, the control group of rats showed rapid increase of both enzymes activities, and this suggests necrosis of hepatocytes. On the other hand, all groups of the rats, which the compounds 1–5 were administered, showed obvious hepatic disorder suppressing effect.

Alphabets (a, b, c, d) shown in FIG. 4 indicate that there are significant differences between group having same alphabets and group having different alphabets statistically, at less than 5% of level of significance (after analysis of variance, a test is carried out by Duncan method as a post statistical test method).

What is claimed is:

1. A method for treating a hepatic disorder, comprising administrating to a living body in need of such treatment a therapeutically effective amount of an extract having at least one ingredient effective to produce a hepatic disorder suppressing effect, wherein the extract is obtained by extracting sarcocarps, pericarps, seeds, leaves, leafstalks, and/or branches of an avocado plant or by extraction of a processed product from sarcocarps, pericarps, seeds, leaves, leafstalks, and/or branches of an avocado plant, with a nonpolar organic solvent.

2. The method according to claim 1, wherein said processed product is obtained by crushing, drying, or concentration.

3. The method according to claim 1, wherein said ingredient is obtained by the steps of 1) extracting sarcocarps, pericarps, seeds, leaves, leafstalks, and/or branches of the avocado plant or extraction of a processed product from sarcocarps, pericarps, seeds, leaves, leafstalks, and/or branches of the avocado plant, with the non-polar organic solvent, 2) fractionating the extract obtained in step 1) by chromatography, and 3) recovering the fraction containing said ingredient, wherein said ingredient has an RF value in a range of between 0.19 and 0.25 when thin-layer chromatography is carried out on a Silica Gel with an organic solvent of 4:1 n-hexane/ethyl acetate as a developing solvent.

4. The method according to claim 1 or 3, wherein the nonpolar organic solvent is one or more selected from the group consisting of n-hexane, cyclohexane, benzene and carbon tetrachloride.

5. The method according to claim 1 or 3, wherein the nonpolar organic solvent is n-hexane.

6. The method according to claim 3, wherein the chromatography is carried out by use of a silica gel column.

* * * * *

UNITED STATES PATENT AND TRADEMARK OFFICE
CERTIFICATE OF CORRECTION

PATENT NO. : 6,942,882 B2
DATED : September 13, 2005
INVENTOR(S) : Arimoto et al.

It is certified that error appears in the above-identified patent and that said Letters Patent is hereby corrected as shown below:

Title page,
Item [62], Related U.S. Application Data, "filed on Mar. 20, 2001" should be
-- filed on Mar. 30, 2001 --.

Column 16,
Line 12, "ingredient has an RF value" should be -- ingredient has an Rf value --.

Signed and Sealed this

Twenty-seventh Day of December, 2005

JON W. DUDAS
*Director of the United States Patent and Trademark Office*